April 26, 1955 C. MALLERIN Plant Pat. 1,384
ROSE PLANT
Filed July 27, 1954
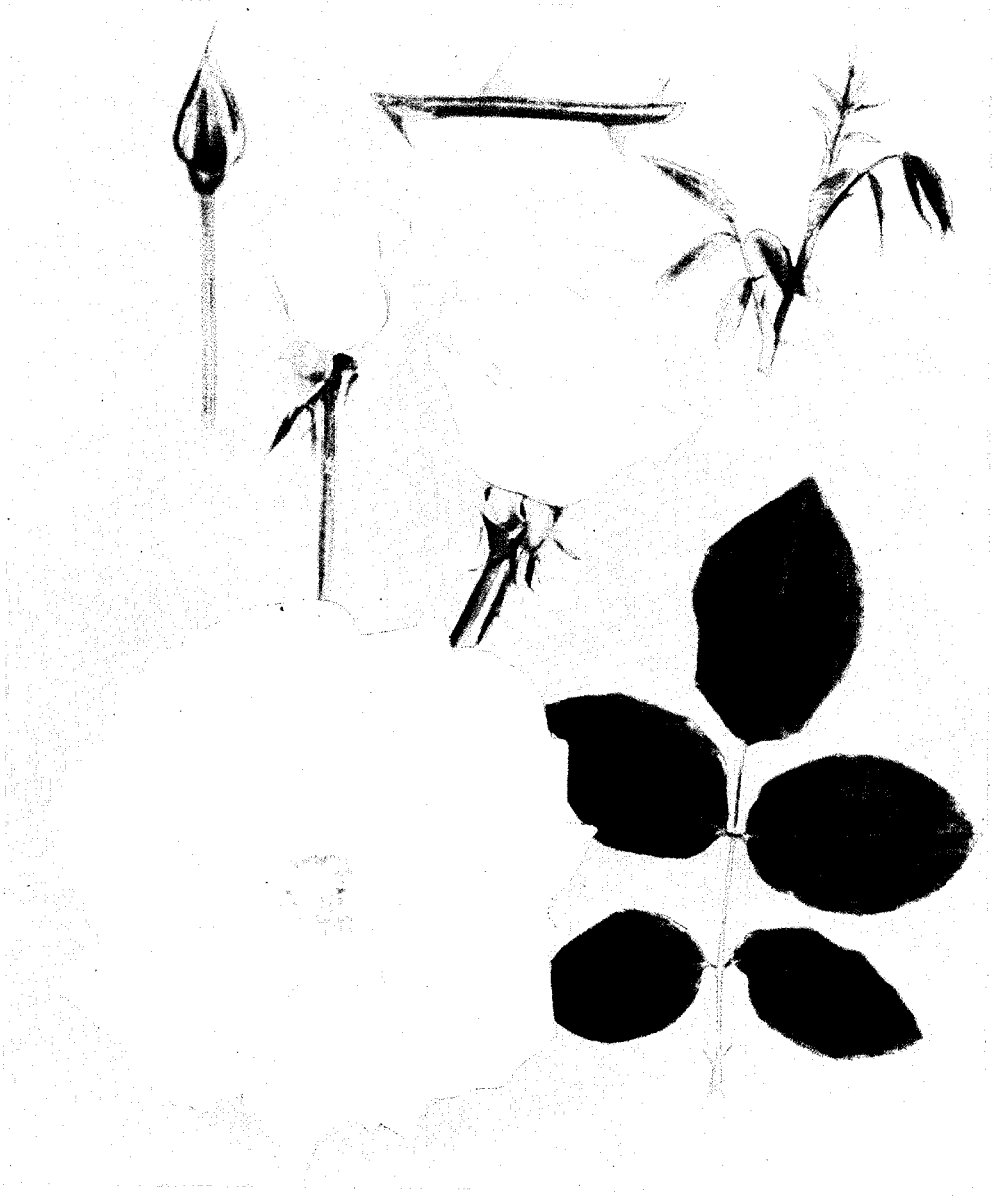
Inventor.
Charles Mallerin
By: Robb & Robb
Attorneys.

United States Patent Office

Plant Pat. 1,384

Patented Apr. 26, 1955

1,384

ROSE PLANT

Charles Malierin, Isere, France, assignor to Jackson & Perkins Company, Newark, N. Y., a corporation of New York Application July 27, 1954, Serial No. 446,188

1 Claim. (Cl. 47—61)

The present invention relates to a new and distinct variety of rose plant of the hybrid tea class, which was originated by me by crossing an unnamed and unpatented seedling of unknown origin with the variety known as "Orange Nassau" (Plant Patent No. 350).

The primary objective in making this cross was to produce a new variety which bears flowers of an attractive color typical of those of the variety "Orange Nassau," combined with healthier and more vigorous habits of growth than is usually characteristic of this parent variety. This objective was fully attained, and as the result thereof, my new variety is particularly characterized by the following unique combination of features:

(1) Healthy and vigorous habits of growth;

(2) An attractive high-centered form of flower similar to the variety known as "Madame Butterfly" (unpatented); and (3) A distinctive and exquisite coloring of the flower petals, with the inside surface of said petals having a general color tonality of Peach Red, overcast with Begonia Red, and with the outside surface of said petals having a general color tonality of Orange Buff, overcast with the Grenadine Pink.

Asexual reproduction of my new variety by budding at Newark, New York, U. S. A., and also at Pleasanton, California, U. S. A., shows that the foregoing characteristics and distinctions come true to form and are established and transmitted through succeeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed seedling of unknown origin.
- *Pollen parent.*—"Orange Nassau."

Classification:
- *Botanic.*—Hybrid tea.
- *Commercial.*—Hybrid tea.

FLOWER (Observations made from specimens grown in a field at Newark, New York, U. S. A. in the early morning during the early part of the month of July.)

Blooming habit: Recurrent—continuous.

Bud:
- *Size.*—Large.
- *Form.*—Ovoid; is not affected by wet or hot weather.
- *Color.*—When sepals first divide—Pomegranate Purple, Plate 12. When petals begin to unfurl—Rose Doree, Plate 1, lightly overcast with Peach Red, Plate 1, and with Apricot Yellow, Plate 4 extending from the base of the petal. When half blown: Inside of petals—Grenadine Pink, Plate 1, lightly overcast with Geranium Pink, Plate 1; reverse of petals—Eosine Pink, Plate 1, overcast with Light Cadmium, Plate 4.
- *Sepals.*—Branched; curl back when petals begin to unfurl.
  - Color: Inside—Kildare Green, Plate 31; outside—Cress Green, Plate 31.

- *Calyx.* — Color — Light Bice Green, Plate 17. Shape—funnel. Size—broad. Aspect—smooth. Odor when rubbed—none.
- *Peduncle.* — Length — medium. Aspect — smooth. Strength—erect; slender. Color—Courge Green, Plate 17.
- *Opening.*—Opens up well; is not affected by adverse weather conditions.

Bloom:
- Size.—Large; average size when fully expanded—4 to 4½ inches.
- *Borne.*—Singly.
- *Stems.*—Medium length; strong.
- *Form (when first open).*—High center.
  - Permanence: Retains its form to the end; outer petals curl back.
- *Petalage.*—Double (full but open center); number of petals under normal conditions—40 to 45.
- *Color.*—Center of flower—Begonia Rose, Plate 1, lightly overcast with Peach Red, Plate 1. Outer petals—Shrimp Pink, Plate 1, lightly overcast with Eosine Pink, Plate 1, and with center of petal overcast with Pale Orange-Yellow, Plate 3. Base of petals (aiglet)—Lemon Chrome, Plate 4. Inside of petals—Peach Red, Plate 1, overcast with Begonia Red, Plate 1. Reverse of petals—Orange Buff, Plate 3, overcast with Grenadine Pink, Plate 2 on the edges of the petals. General tonality from a distance—Peach Red, Plate 1, overcast with Begonia Red, Plate 1.
- *Discoloration.*—General tonality at end of first day—Peach Red, Plate 1, overcast with Begonia Red, Plate 1. Second day—Peach Red, Plate 1, lightly overcast with Begonia Red, Plate 1. Third day—Peach Red, Plate 1, overcast with Eosine Pink, Plate 1.

Petals:
- *Texture.*—Thick; is not affected by wet or hot weather.
- *Appearance.*—Inside—satiny. Outside—shiny.
- *Form.*—Oval.
- *Arrangement.*—Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—long. As cut flower—long.

GENITAL ORGANS

Stamens, anthers: Medium size; many; regularly arranged around styles. Color—Salmon Orange, Plate 2.

Stamens, filaments (threads): Medium length. Color—Mikado Orange, Plate 3.

Pollen: Color—Light Salmon-Orange, Plate 2.

Styles: Bunched; uneven length; short; thin.

Stigmas: Color—Buff Yellow, Plate 4.

Ovaries: All enclosed in calyx.

Hips: None.

Seeds: None.

PLANT

Form: Bush.

Growth: Vigorous; upright.

Foliage 5 to 7 leaflets.
- *Size.*—Medium.
- *Quantity.*—Abundant.
- *Color.*—New foliage: Upper side—Yellowish Oil Green, Plate 5, overcast with Garnet Brown, Plate 1; under side—Hay's Russet, Plate 14. Old foliage: Upper side—Deep Dull Yellow Green, Plate 32; under side—Absinthe Green, Plate 31.
- *Shape.*—Oval pointed.
- *Texture.*—Upper side—leathery. Under side—smooth.
- *Ribs and veins.*—Ordinary.
- *Edge.*—Serrated (saw-toothed).
- *Serration.*—Double and single; small.
- *Leaf stem.*—Color—Kildare Green, Plate 31. Under side—prickles.
- *Stipules.*—Medium length; bearded.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: On main stalks from base—ordinary; on laterals from stalk—ordinary. Form—flat base; medium length; hooked downward. Color (when young)—Deep Chrysolite Green, Plate 31. Position—irregular.

*Prickles.*—Quantity: On main stalks—none; on laterals—none.

*Short needles.*—Quantity: On main stalks—none; on laterals—none.

I claim:

A new and distinct variety of rose plant of the hybrid tea class, substantially as herein shown and described, characterized particularly as to novelty by its healthy and vigorous habits of growth, by the attractive high-centered form of its flowers similar to those of the variety "Madame Butterfly" (unpatented), by the Peach Red general color tonality overcast with Begonia Red of the inside surface of the flower petals in its fully open flowers, and by the Orange Buff general color tonality overcast with Grenadine Pink of the outside surface of said petals.

No references cited